United States Patent

Aono (10) Patent No.: US 9,588,088 B2
(45) Date of Patent: Mar. 7, 2017

(54) GAS SAMPLE INTRODUCTION DEVICE

(71) Applicant: SHIMADZU CORPORATION, Kyoto-shi, Kyoto (JP)

(72) Inventor: Akira Aono, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 381 days.

(21) Appl. No.: 13/966,765

(22) Filed: Aug. 14, 2013

(65) Prior Publication Data

US 2015/0047442 A1    Feb. 19, 2015

(51) Int. Cl.
| | |
|---|---|
| *G01N 1/22* | (2006.01) |
| *G01N 30/20* | (2006.01) |
| *G01N 30/02* | (2006.01) |
| *G01N 30/08* | (2006.01) |

(52) U.S. Cl.
CPC ........... *G01N 30/20* (2013.01); *G01N 1/2214* (2013.01); *G01N 2030/025* (2013.01); *G01N 2030/085* (2013.01); *G01N 2030/207* (2013.01)

(58) Field of Classification Search
CPC .. G01N 27/407; G01N 27/4077; G01N 30/12; G01N 2030/025; G01N 30/24; G01N 30/461; G01N 30/30; G01N 2001/2223; G01N 33/0011; G01N 35/1095; G01N 30/20; G01N 35/1097; G01N 1/24; G01N 1/2258; G01N 1/22; G01N 1/2214; G01M 15/102; B01J 2220/54

USPC ....... 73/23.31, 23.41, 864.81, 23.39, 864.83, 73/863.12
See application file for complete search history.

(56) References Cited

U.S. PATENT DOCUMENTS

| | | | |
|---|---|---|---|
| 6,029,499 A * | 2/2000 | Sittler et al. ................. | 73/23.42 |
| 8,584,507 B2 * | 11/2013 | Aono ........................... | 73/23.41 |
| 2003/0172718 A1 * | 9/2003 | Lee et al. ..................... | 73/23.41 |
| 2010/0107730 A1 * | 5/2010 | Aono ..................... | G01N 30/12 73/23.39 |

FOREIGN PATENT DOCUMENTS

JP        7-103956 A    4/1995

* cited by examiner

*Primary Examiner* — Laura Martin
*Assistant Examiner* — Truong Phan
(74) *Attorney, Agent, or Firm* — Sughrue Mion, PLLC

(57) ABSTRACT

In a gas sample analysis device including a metering tube, sample gas supply channel, carrier gas supply channel, evacuation channel and collection tube, there is provided a first channel switching valve which switches between a load state in which the metering tube is interposed between said sample gas supply channel and the evacuation channel and an injection state in which the metering tube is interposed between the sample gas supply channel and gas analysis device; and a second channel switching valve which, in the load state or injection state, switches between a collection tube interposition state in which the collection tube is interposed between the sample gas supply channel and the metering tube or between the metering tube and the gas analysis device, and a collection tube shunt state in which the collection tube is not interposed.

3 Claims, 4 Drawing Sheets

GAS SAMPLE INTRODUCTION DEVICE

FIELD OF THE INVENTION

The present invention relates to a gas sample introduction device for introducing sample gas into a gas analysis device such as a gas chromatography device.

BACKGROUND OF THE INVENTION

Gas sample introduction devices for introducing a sample gas into the carrier gas flow supplied to the analytical column are widely used in gas chromatography analysis on gas samples. For sample introduction by this sort of gas sample introduction device, there is the scheme whereby a predetermined quantity of sample gas is metered by a metering tube provided in the channel and introduced into the analytical column, and the scheme whereby the sample gas is concentrated by a concentrating device provided in the channel and introduced into the analytical column, and devices are widely used which switch between and execute both schemes.

Figure 4:
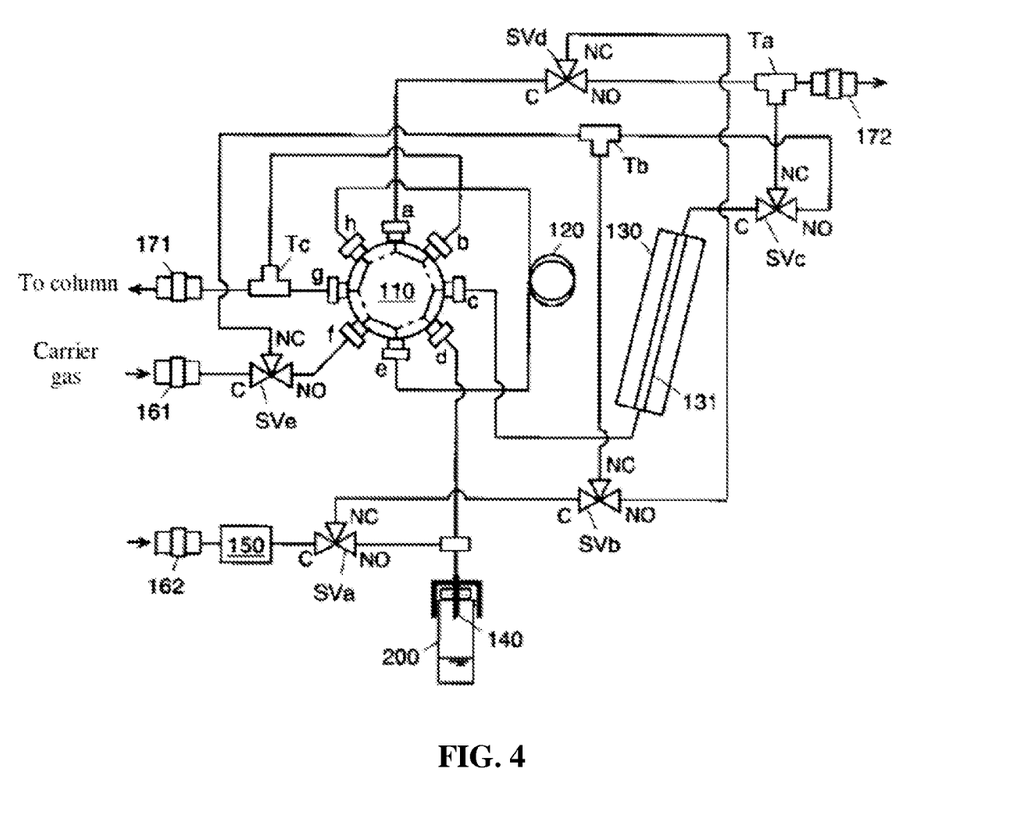
FIG. 4—A simplified diagram showing an example of a conventional gas sample introduction device.

FIG. 4 illustrates the channel configuration of a conventional gas sample introduction device equipped with a function of switching between and executing sample introduction employing a metering tube (referred to below as metering mode) and sample introduction employing a concentrating device (referred to below as concentrating mode), as mentioned above. Eight-way valve 110 allows switching, by manual force or mechanical force, between two states: the connection state shown by a solid line and the connection state shown by a dotted line in FIG. 4. SVa through SVe are solenoid valves and Ta through Tc are branch tubes. It will be noted that, for each solenoid valve, NO signifies a normally open port, NC signifies a normally closed port, and C signifies a common port. It will be noted that gas inlet 162 and mass flow controller 150 serve to supply gas for pressurization of sample container 200 or gas for dry purging of concentrating device 130 at a predetermined flow rate, the details of which will be omitted here.

First, the operation of the metering mode in the device of FIG. 4 will be described. When the eight-way valve 110 is placed into the connection state shown by the dotted line and the solenoid valves SVd and SVe are switched to the NO side (i.e. the C side and NO side are connected), sample gas taken up from sample container 200 by needle 140 passes via ports d and e through metering tube 120, and is then discharged via ports h and a and solenoid valve SVd and branch tube Ta through gas outlet 172. Carrier gas supplied into gas inlet 161 from an unillustrated gas bottle or the like is fed into the analytical column via solenoid valve SVe, ports f and g, branch tube Tc and gas outlet 171.

With sample gas having flowed into the metering tube 120 in this manner, the eight-way valve 110 is switched to the connection state shown by a solid line in FIG. 4. As a result, the carrier gas starts to pass via ports f and e through metering tube 120, a set quantity of sample gas determined by the inside volume of metering tube 120, which was held in metering tube 120, is pushed out by the carrier gas and is fed via ports h and g and branch tube Tc toward the analytical column. It will be noted that the sample gas fed to the analytical column is divided into components in the process of passing through the column, and is successively detected by a detector as it comes out of the column.

Next, the operation of the concentrating mode will be described. When the eight-way valve 110 is placed into the connection state shown by a solid line and solenoid valve SVe is switched to the NO side and solenoid valve SVc to the NC side, sample gas collected by needle 140 passes via ports d and c through collection tube 131 provided in concentrating device 130, and is then discharged via solenoid valve SVc and branch tube Ta from gas outlet 172. Here, the collection tube 131 is cooled by an unillustrated cooling means, and in the process of the sample gas passing through the collection tube 131, predetermined components in the sample gas (sample components) are adsorbed inside the collection tube 131. It will be noted that the carrier gas supplied from gas inlet 161 here flows via solenoid valve SVe, ports f and e, metering tube 120, ports h and g, branch tube Tc and gas outlet 171 into the analytical column.

After the sample components have been adsorbed inside the collection tube 131 in this manner, the eight-way valve 110 is switched to the connection state shown by the dotted line, solenoid valve SVc is switched to the NO side, and solenoid valve SVe is switched to the NC side. Thereupon, the carrier gas starts to pass via solenoid valve SVe, branch tube Tb and solenoid valve SVc and through the collection tube 131 in the opposite direction to the sample gas previously. In this state, when the collection tube 131 is rapidly heated by an unillustrated heating means, the sample components which have been adhered inside the collection tube 131 are released at once, and the sample components at high concentration are carried by the carrier gas and flow out from collection tube 131, pass through ports c and b and branch tube Tc and are introduced into the analytical column. In this way, with the concentrating mode, even if the sample components are contained in the original sample gas in trace amounts, they can be fed into the analytical column after concentrating to increase their concentration, thus providing the effect of increasing the detection sensitivity.

In a conventional gas sample introduction device equipped with a function of switching between metering mode and concentrating mode as above, the metering tube 120 and collection tube 131 are connected in parallel, and sample gas fed out from one of these flows into the analytical column. Furthermore, all of the gas taken up into the metering tube 120 is introduced into the analytical column.

Patent literature 1—Japanese Unexamined Patent Application Publication H7-103956

In gas chromatography, a technique called the pre-cut method is known, whereby specific components are separated and removed from the sample gas before introduction into the analytical column (for example, see Patent literature 1). With the pre-cut method, the sample gas is taken up into the metering tube, after which a pre-column is interposed between the metering tube and analytical column and the sample gas inside the metering tube is introduced into the pre-column. The target component (generally, the low boiling point component) eluted first from the pre-column is introduced into the analytical column, after which the pre-column is disconnected from the analytical column before the unnecessary components (generally, high boiling point components) remaining in the pre-column are introduced into the analytical column. As a result, the unnecessary high boiling point components can be prevented from being introduced into the analytical column, which allows one to shorten the analysis time and to do without increasing the temperature of the analytical column, thus having the advantage of allowing one to extend the lifetime of the analytical column.

However, in order to execute this sort of pre-cut method in a conventional gas sample introduction device equipped with a function of switching between metering mode and concentrating mode as described above, it is necessary to provide a pre-column and dedicated channel switching system for pre-cut operation as described above in addition to the metering tube and collection tube, so the configuration of the device become more complicated, leading to increased size and higher cost of the device.

The present invention was made in view of this point, its object being to provide a gas sample introduction device capable of switching between and executing a metering mode and concentrating mode, which allows one to perform sample introduction by the pre-cut method without providing the aforementioned pre-column and dedicated channel switching system for pre-cut operation.

SUMMARY OF THE INVENTION

The gas sample introduction device according to an aspect of the present invention, made to resolve the aforementioned problem, is a gas sample introduction device for introducing sample gas into a gas analysis device, including:

a) a metering tube having a predetermined volume;

b) a sample gas supply channel for introducing sample gas into said metering tube;

c) a carrier gas supply channel for introducing carrier gas into said metering tube;

d) an evacuation channel for discharging gas which has passed through said metering tube to the outside;

e) a concentrating means which comprises a collection tube containing an adsorbent and concentrates the sample gas through thermal desorption;

f) a first channel changeover valve which switches between a load state in which said metering tube is interposed between said sample gas supply channel and said evacuation channel and an injection state in which said metering tube is interposed between said carrier gas supply channel and said gas analysis device; and g) a second channel switching valve which, in said load state or injection state, switches between a collection tube interposition state in which said collection tube is interposed between said sample gas supply channel and metering tube or between said metering tube and gas analysis device, and a collection tube shunt state in which said collection tube is not interposed.

Based on the above-described configuration, it is possible to switch between a state where the metering tube and collection tube are connected in series and a state where they are connected in parallel, and furthermore, when the sample which has been taken up into the metering tube is to be introduced into the gas analysis device, such as a gas chromatography device, the collection tube can be connected to the downstream side of the metering tube. Thus, the sample gas which has been taken up into the metering tube can be introduced into the gas analysis device after crude separation has been performed through interaction with the adsorbent in the collection tube. Here, when the components to be analyzed have been eluted from the collection tube and introduced into the gas analysis device, by disconnecting the collection tube from the carrier gas channel, unnecessary components eluted from the collection tube later than the components to be analyzed can be eliminated (i.e. pre-cut) without introducing them into the gas analysis device. In other words, in the present invention, in a gas sample introduction device comprising a metering tube and a collection tube for sample concentration, the collection tube is additionally made to function as a pre-column as described above, thereby making it possible to perform sample introduction by the pre-cut method (referred to below as pre-cut mode) without providing a pre-column or a dedicated channel switching system for pre-cut operation.

When pre-cut mode is to be executed in the gas sample introduction device according to the present invention having the configuration described above, the second channel switching valve is placed in the collection tube shunt state, and the first channel switching valve is placed in a load state. As a result, a channel is formed going from the sample gas supply channel via the metering tube to the evacuation channel, and the inside of the metering tube is filled with sample gas (in other words, sample gas is taken up into the metering tube). Subsequently, the first channel switching valve is placed in the injection state and the second channel switching valve is placed in the collection tube interposition state. As a result, a channel going from the carrier gas supply channel through the metering tube and collection tube into the gas analysis device is formed, and the sample gas inside the metering tube is introduced along with carrier gas into the collection tube and subjected to component separation. The components to be analyzed within the sample gas are then eluted from the collection tube and introduced into the gas analysis device, after which, in a state where some of the separated components (components which do not need to be analyzed) remain in the collection tube, the second channel switching valve is switched to the collection tube shunt state. As a result, the collection tube is disconnected from the carrier gas channel, and the unnecessary components are pre-cut.

It will be noted that when metering mode is to be executed, after the second channel switching valve has been placed in the collection tube shunt state, the first channel switching valve is first placed in the load state. As a result, a channel is formed from the sample gas supply channel via the metering tube to the evacuation channel, and the sample gas passes through the metering tube. Subsequently, when the first channel switching valve is placed in the injection state, a channel is now formed from the carrier gas supply channel via the metering tube to the gas analysis device, and thus the sample gas which had filled the inside of the metering tube is carried by the carrier gas and introduced into the gas analysis device.

Furthermore, when the concentrating mode is to be executed, after the second channel switching valve has been placed into the collection tube interposition state, the first channel switching valve is first placed in the load state. As a result, a channel is formed from the sample gas supply channel through the collection tube and further through the metering tube and to the evacuation channel. Here, by cooling the collection tube with a predetermined cooling means, predetermined components in the sample gas passing through the collection tube are adsorbed inside the collection tube. It will be noted that adsorption of predetermined components may also be carried out at ambient temperature without providing a cooling means. Subsequently, when the first channel switching valve is placed in the injection state, a channel is formed from the carrier gas supply means via the metering tube and collection tube to the gas analysis device. Here, by rapidly increasing the temperature of the collection tube with a predetermined heating means, sample components which have been adsorbed inside the collection tube are desorbed, and those sample components are carried by the carrier gas and introduced into the gas analysis device.

It will be noted that the channel switching operation by the first channel switching valve and/or second channel switching valve may also be performed manually by the user, or the operation may take place in response to user instructions or a predetermined program using a driving means such as a motor.

The gas sample introduction device according to the present invention as described above can also include h) a purging gas supply channel for introducing a purging gas into said collection tube; and i) a purging gas discharge channel for discharging the purging gas which has passed through said collection tube to the outside, wherein said second channel switching valve interposes said collection tube between said purging gas supply channel and purging gas discharge channel in said collection tube shunt state.

Based on this sort of configuration, after sample introduction, in a state where the collection tube is shunted from the carrier gas channel (i.e. the channel running from the carrier gas supply channel to the gas analysis device), the sample components remaining in the collection tube are discharged to the outside by the purging gas.

Based on the gas sample introduction device according to the present invention, as described above, in a gas sample introduction device comprising a metering tube and a collection tube for sample concentration, the collection tube can be made to additionally function as an aforesaid pre-column. Thus, sample introduction can be performed by the pre-cut method without providing a separate pre-column or a dedicated channel switching system for pre-cut operation.

DETAILED DESCRIPTION OF THE EXEMPLARY EMBODIMENT

Figure 1:
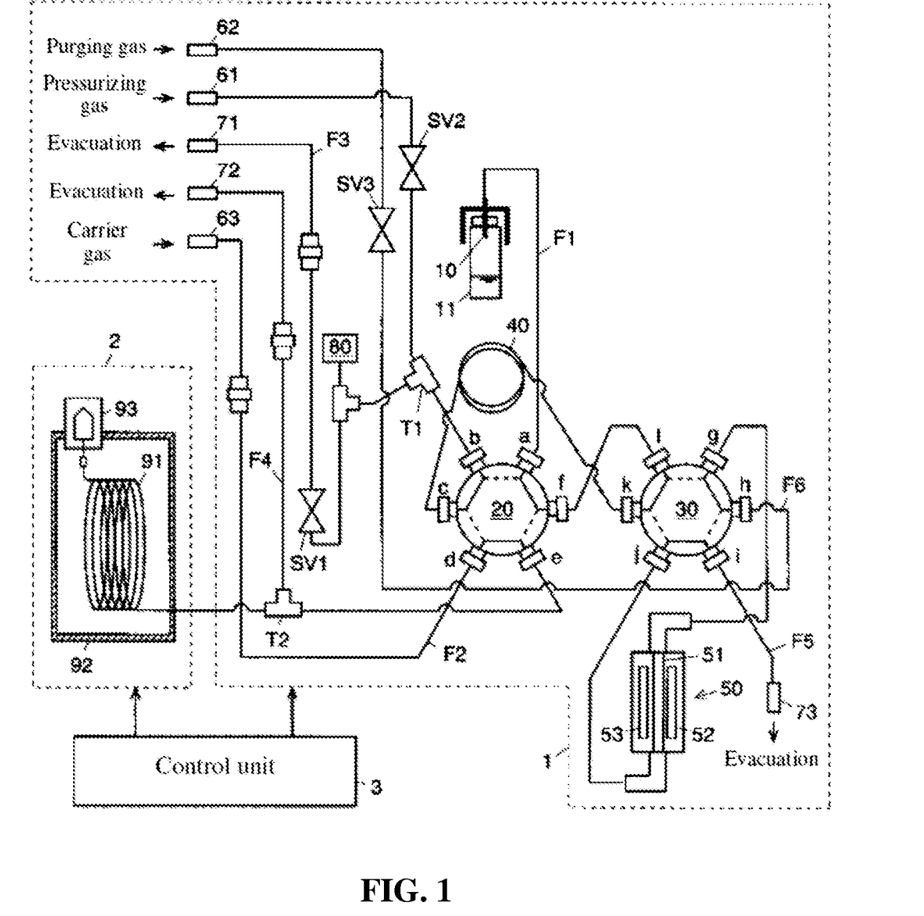
FIG. 1—A simplified diagram of a gas chromatograph using a gas sample introduction device according to an example of embodiment of the present invention.

An example of embodiment of the gas sample introduction device according to the present invention will be described below with reference to the drawings. FIG. 1 is a diagram of a gas chromatograph using a gas sample introduction device of the present example of embodiment.

The gas chromatograph according to the present example of embodiment, as shown in FIG. 1, broadly speaking, consists of a sample introduction unit 1, an analysis unit 2 and a control unit 3. Sample introduction unit 1 contains two channel switching valves 20 and 30, a metering tube 40 and a sample concentrating unit 50, and analysis unit 2 contains a column oven 92, an analytical column 91 and a detector 93.

In sample introduction unit 1, first channel switching valve 20 and second channel switching valve 30 are rotary 6-port 2-position valves having six ports, i.e. ports a through f or ports g through l, respectively, which switch alternatively between the connection state shown by the solid line and the connection state shown by the dotted line in FIG. 1 under the control of control unit 3. It will be noted that in the first channel switching valve 20, the state shown by a solid line in FIG. 1 corresponds to the load state in the present invention, and the state shown by a dotted line corresponds to the injection state. Furthermore, in the second channel switching valve 30, the state shown by a solid line in FIG. 1 corresponds to the collection tube shunt state in the present invention, and the state shown by the dotted line corresponds to the collection tube interposition state.

A needle 10 for taking up the sample gas is connected to port a of first channel switching valve 20, and needle 10 is arranged such that its tip is located in the space above the sample container 11 (head space). A gas inlet 61 for introducing gas (pressurizing gas) for pressurizing the inside of the sample container 11 and a gas outlet 71 for discharging sample gas are connected to port b via branch tube T1. A solenoid valve SV2 is provided in the channel going from branch tube T1 to gas inlet 61, and a pressure sensor 80 and solenoid valve SV1 are provided in the channel going from branch tube T1 to gas outlet 71. Port c is connected to port k of second channel switching valve 30 via a metering tube 40 having a predetermined volume. Port d is connected to gas inlet 63 for introducing carrier gas, and port e is connected via branch tube T2 to the inlet end of column 91 and split channel F4. Split channel F4 serves for discharging a portion of the sample gas without feeding it to column 91 and has a gas outlet 72 for discharging sample gas provided at its end. Port f is connected to port l of second channel switching valve 30.

Furthermore, collection tube 51 of sample concentrating unit 50 is connected between port g and port j of second channel switching valve 30, gas inlet 62 for introducing the purging gas, described below, is connected via solenoid valve SV3 to port h, and gas outlet 73 for discharging the purging gas is connected to port i. It will be noted that while a split system was used for the sample introduction unit 1 here, a splitless system may of course be used as well.

For the collection tube 51, it is possible to use a hollow tube coated on its inside surface with a predetermined adsorbent or a hollow tube filled inside with a predetermined adsorbent. As the predetermined adsorbent, for example, activated carbon, various types of resins and the like can be used. In addition to this sort of collection tube 51, the sample concentrating unit 50 comprises a cooling unit 52 for cooling the collection tube 51 and a heating unit 53 for heating the collection tube 51. Heating unit 53 can be fashioned for example from a heater or the like provided so as to connect to the collection tube 51, and the cooling unit 52 can for instance cool the collection tube 51 by passing through a predetermined coolant inside a coolant tube provided so as to contact the collection tube 51, or perform cooling by means of a Peltier element.

In the sample introduction unit 1, channel F1 connected to port a and channel F2 connected to port d of first channel switching valve 20 correspond respectively to the sample gas supply channel and carrier gas supply channel of the present invention, and channel F3 going from port b to gas outlet 71 corresponds to the evacuation channel of the present invention. Moreover, channel F6 connected to port h of second channel switching valve 30 corresponds to the purging gas supply channel of the present invention and channel F5 connected to port i corresponds to the purging gas discharge channel of the present invention. Furthermore, analysis unit 2 corresponds to the gas analysis device of the present invention.

It will be noted that gas inlets 61, 62 and gas outlet 71 are connected to an unillustrated pressure control unit, and the pressure of gas flowing through gas inlets 61, 62 and gas outlet 71 is controlled by the pressure control unit. Furthermore, gas inlet 63 and gas outlets 72, 73 are controlled by an unillustrated flow rate control unit, and the flow rate of gas flowing through gas inlet 63 and gas outlets 72, 73 is controlled by said flow rate control unit. It will be noted that the aforesaid pressure control unit and flow rate control unit may be either of the electronically controlled type or manual type.

Control unit 3 controls the opening and closing operation of solenoid valves SV1 through SV3 of sample introduction unit 1, switching operation of channel switching valves 20 and 30, and operation of the pressure control unit, flow rate control unit, etc., and also controls operation of column oven 92 and detector 93 of analysis unit 2. Control unit 3 is implemented for instance by means of a personal computer, and sample introduction into analysis unit 2 by sample introduction unit 1 and analysis of samples by analysis unit 2 are executed by controlling the operation of the aforementioned units according to a predetermined control program.

Sample introduction unit 1 according to the present example of embodiment performs introduction of sample gas by the head space method. The head space method is a technique whereby a liquid sample (or solid sample) held inside sample container 11 is heated and volatilized sample components are sampled from the upper space inside the container and introduced into the column 91. Furthermore, sample introduction unit 1 according to the present example of embodiment has a configuration that allows selective execution of metering mode, concentrating mode and pre-cut mode as the operating mode at the time of sample gas introduction. The operating mode to be executed is designated in advance by the user. The operation of the sample introduction unit 1 at the time of execution of each of the aforementioned modes will be described below. It will be noted that solenoid valves SV1 through 3 are closed unless specified otherwise.

1. Metering Mode

Metering mode is a mode in which sample gas is metered by metering tube 40, after which the entire quantity thereof is introduced into the analytical column 91. During execution of this metering mode, usually, by placing the second channel switching valve 30 into the connection state shown by a solid line, the series of operations described below is performed in a state where collection tube 51 has been shunted from the sample gas and carrier gas channel.

(i) Pressurization Process

First, the first channel switching valve 20 is placed in the connection state shown by a solid line, and then sample container 11 is heated to a predetermined temperature by an unillustrated heating means and placed in a state of gas-liquid equilibrium. Subsequently, solenoid valve SV2 is opened and the inside of sample container 11 is pressurized by introducing a pressurizing gas through gas inlet 61.

(ii) Process of Introducing Sample Gas Into Metering Tube

Next, when solenoid valve SV2 is closed and solenoid valve SV1 is opened, gas containing sample components which have gasified inside the sample container 11 (sample gas) flows into channel F1 through needle 10, passes through first channel switching valve 20 and second channel switching valve 30, and flows into metering tube 40. Here, a portion of the gas which has flowed into metering tube 40 is discharged via first channel switching valve 20, branch tube T1 and channel F3 through gas outlet 71. It will be noted that during the above process, carrier gas sequentially passes from gas inlet 63 through channel F2→first channel switching valve 20→branch tube T2 and into column 91.

(iii) Process of Feeding Sample Gas to Column

Subsequently, when the first channel switching valve 20 is placed in the connection state shown by a dotted line, carrier gas supplied through gas inlet 63 passes sequentially through channel F2→first channel switching valve 20→metering tube 40→second channel switching valve 30→first channel switching valve 20→branch tube T2 and flows into column 91. As a result, a predetermined quantity of sample gas held in the metering tube 40 is introduced to column 91 along with the flow of the carrier gas. It will be noted that a portion of the carrier gas and sample gas which has flowed out of port e of first channel switching valve 20 and reached branch tube T2 flows into split channel F4 at a predetermined split ratio and is discharged from gas outlet 72.

2. Concentrating Mode

Next, the operation during execution of concentrating mode will be described. Concentrating mode is a mode in which sample gas is concentrated by sample concentrating unit 50 and then introduced into column 91.

(i) Pressurization Process

First, the first channel switching valve 20 and second channel switching valve 30 are placed in the connection state shown by a solid line, and then solenoid valve SV2 is opened and heating and pressurization of sample container 11 are performed in the same manner as in the metering mode described above.

(ii) Sample Component Adsorption Process

Subsequently, solenoid valve SV2 is closed, the second channel switching valve 30 is switched to the connection state shown by a dotted line, and solenoid valve SV1 is opened. As a result, the sample gas inside the sample container 11 passes through needle 10→channel F1→first channel switching valve 20→second channel switching valve 30 in that order and flows into collection tube 51. Here, the collection tube 51 is cooled to a predetermined temperature by a cooling unit 52, and sample components are adsorbed inside the collection tube 51 in the process of the sample gas passing through the collection tube 51. It will be noted that sample gas after sample components have been adsorbed flows in sequence through second channel switching valve 30→metering tube 40→first channel switching valve 20→branch tube T1→channel F3 and is discharged from gas outlet 71.

(iii) Dry Purging Process

In the sample component adsorption process described above, water inside the sample gas is adsorbed inside the collection tube 51 along with the sample components to be analyzed, so in order to keep that water from being fed into the column 91 at the time of analysis, it is necessary to perform a water removal process (dry purging) in advance. In this dry purging process, the second channel switching valve 30 is switched to the connection state shown by the solid line and solenoid valve SV3 is opened to form a channel running from gas inlet 62 through collection tube 51 to gas outlet 73. As a result, the purging gas, such as dry helium gas, passes through the channel and the water inside the collection tube 51 is discharged through gas outlet 73 along with the purging gas.

(iv) Process of Sample Component Desorption and Feeding Into Column

Subsequently, the first channel switching valve 20 and second channel switching valve 30 are switched to the connection state shown by the dotted line, and the collection tube 51 is rapidly heated with a predetermined timing by heating unit 53 to cause the sample components to be desorbed from the collection tube 51. As a result, after passing through channel F2→first channel switching valve 20→metering tube 40→second channel switching valve 30→collection tube 51, the carrier gas supplied from gas inlet 63 flows through the second channel switching valve 30→first channel switching valve 20→branch tube T2 and into column 91, and sample components desorbed from collection tube 51 through heating by the heating unit 53 are introduced into the column 91 together with the carrier gas.

3. Pre-cut Mode

Next, the operation during execution of pre-cut mode will be described. Pre-cut mode in the present example of embodiment is a mode whereby sample gas which has been taken up into the metering tube 40 undergoes crude separation in the collection tube 51, and a portion of it is introduced into the column 91.

(i) Pressurization Process

First, the first channel switching valve 20 and second channel switching valve 30 are placed into the connection state shown by the solid line, after which solenoid valve SV2 is opened, and heating and pressurization of the sample container 11 is performed in the same manner as in the metering mode described above.

(ii) Process of Sample Gas Introduction Into Metering Tube

Next, in the same way as in the metering mode described above, solenoid valve SV2 is closed and solenoid valve SV1 is opened to cause the sample gas, gasified inside the sample container 11, to flow into the metering tube 40.

(iii) Process of Feeding Sample Gas to Column

Next, when the first channel switching valve 20 and second channel switching valve 30 are switched to the connection state shown by the dotted line, carrier gas supplied through gas inlet 63 passes through channel F2→first channel switching valve 20→metering tube 40→second channel switching valve 30→collection tube 51, and further flows through second channel switching valve 30→first channel switching valve 20→branch tube T2 and into column 91. This flow of carrier gas causes the sample gas filled into metering tube 40 to be pushed out and flow into collection tube 51. Here, the temperature of collection tube 51 is room temperature (i.e. a state where neither cooling by cooling unit 52 nor heating by heating unit 53 is being carried out), and the various components in the sample gas introduced into collection tube 51 are separated into individual components through interaction with the adsorbent inside the collection tube 51. The sample components separated in this manner are eluted from collection tube 51 in order from lowest to highest boiling point and introduced into column 91 together with carrier gas.

(iv) Pre-cut Process

Subsequently, when a particular preset period of time (hereinafter referred to as "pre-cut time") has elapsed, the first channel switching valve 20 and second channel switching valve 30 are switched to the state shown by a solid line. As a result, the metering tube 40 and collection tube 51 are shunted from the carrier gas channel, and carrier gas starts to flow from gas inlet 63 via channel F2→first channel switching valve 20→branch tube T2 into column 91. Thus, the components remaining inside the collection tube 51 at this time come to be excluded from the carrier gas channel without being introduced into the column 91. Therefore, the time when the target component inside the sample gas is to be introduced into the column 91 is determined in advance through preparatory experiments or the like, and the pre-cut time is set such that pre-cut will be performed with an appropriate timing from that time onward, thus making it possible to introduce only the low boiling pointing component containing the target component into the column 91 and cut the unnecessary high boiling point components.

In this pre-cut mode, it is preferable to set the parameters (pre-cut time, carrier gas flow rate, etc.) so that the target component and unnecessary high boiling point components can be adequately separated and so that sample introduction can be completed as quickly as possible. While component separation with the collection tube 51 was performed with the collection tube 51 at room temperature in the above example, it will be noted that component separation with the collection tube 51 may also be performed with the collection tube 51 having been adjusted to a predetermined temperature by the cooling unit 52 and heating unit 53. As a result, it becomes possible to set more appropriate parameters. Furthermore, the cooling unit 52 and heating unit 53 are conventionally provided in the sample concentrating unit 50 and do not require the addition of new parts.

(v) Purging Process

After performing the pre-cut process above and before the next sample is introduced, the collection tube 51 is purged and the high boiling point components remaining in the collection tube 51 are discharged outside the system. In this purging process, in a state where the first channel switching valve 20 and second channel switching valve 30 have been placed in the connection state shown by a solid line, solenoid valve SV3 is opened and collection tube 51 is further heated by heating unit 53 to cause desorption of high boiling point components from the collection tube 51. As a result, purging gas such as a helium gas supplied through gas inlet 62 passes through solenoid valve SV3 and flows through second channel switching valve 30→collection tube 51→second channel switching valve 30→gas outlet 73 in that order, and the high boiling point components desorbed from the collection tube 51 due to heating by the heating unit 53 are discharged together with purging gas through the gas outlet 73 outside the system.

Figure 2:
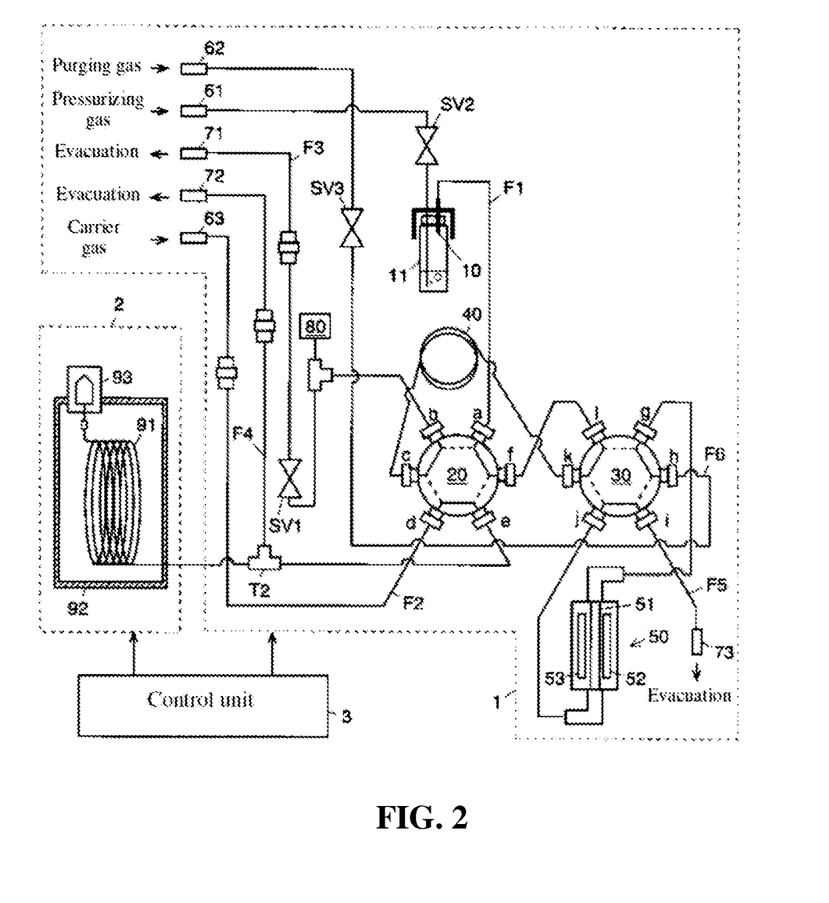
FIG. 2—A simplified diagram of a gas chromatograph using a gas sample introduction device according to another example of embodiment of the present invention.
Figure 3:
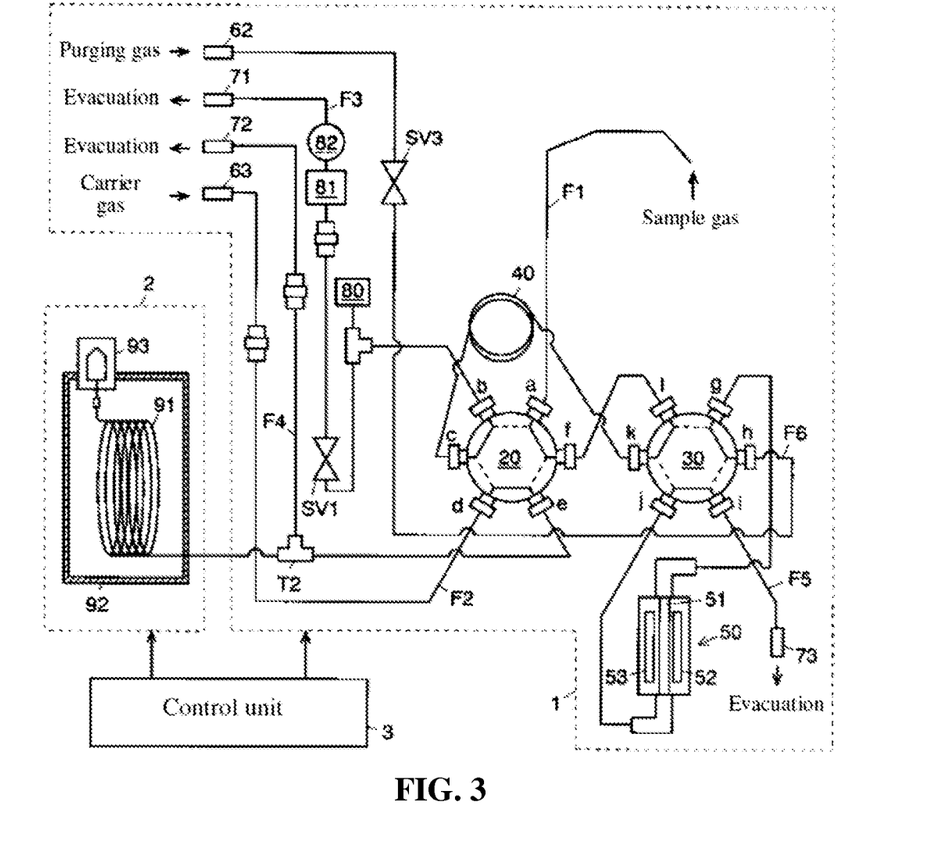
FIG. 3—A simplified diagram of a gas chromatograph using a gas sample introduction device according to another example of embodiment of the present invention.

The best mode for embodying the present invention was described above using an example of embodiment; the present invention is however not limited to the example of embodiment described above, and can be suitably modified within the gist of the present invention. For example, in the example of embodiment described above, introduction of sample gas was performed by the head space method, but the sample introduction method is not limited thereto, and various schemes can be used. FIGS. 2 and 3 show configuration examples of a gas chromatograph comprising a gas sample introduction device based on another sample introduction scheme.

FIG. 2 is a scheme in which purging gas is blown into a sample liquid to forcibly drive out and collect volatile organic compounds, mold odor, etc. in water. In this example, there is no branch tube T1, and the other end of the channel connected to gas inlet 61 is inserted into sample container 11. The rest of the configuration is the same as in the example of embodiment described above. In a sample introduction device having such a configuration, in metering mode, concentrating mode and pre-cut mode, bubbling (aeration) of the sample liquid is performed in the above-described "(i) Pressurization process." Specifically, when the first channel switching valve 20 is placed in the connection state shown by a solid line in FIG. 2 and solenoid valve SV2 is opened, pressurizing gas is introduced through gas inlet 61 and passed through the sample liquid. As a result, volatile organic compounds, etc. in the liquid are driven out into the upper space of the sample container 11, and the inside of the sample container 11 is pressurized.

Subsequent operation is the same as in the previously described example of embodiment.

Furthermore, FIG. 3 is a scheme in which sample gas is suctioned and collected with a pump. The device in this drawing has the same configuration as in the example of embodiment described above, except for the point that it does not have a channel for pressurizing the sample container (a channel going from gas inlet 61 to branch pipe T1 in FIG. 1) and the point of having a pump 82 for suctioning sample gas between solenoid valve SV1 and gas outlet 71 and a mass flow controller 81 for controlling the flow rate of the suctioning. When metering mode or pre-cut mode is executed in a sample introduction device having this sort of configuration, "(ii) Process of introducing sample gas into metering tube" is performed without performing the "(i) Pressurization process" described above. Here, the first channel switching valve 20 and second channel switching valve 30 are placed in the connection state shown by the solid line in FIG. 3, solenoid valve SV1 is opened, and pump 82 is driven. As a result, the sample gas contained in the sample container (not illustrated), such as a sample bag, is suctioned via channel F1 connected to port a of first channel switching valve 20, passes through metering tube 40 and is discharged from gas outlet 71. Furthermore, when executing the concentrating mode, "(ii) Sample component adsorption process" is performed without performing the "(i) Pressurization process" described above. Here, the first channel switching valve 20 is placed in the connection state shown by a solid line in FIG. 3, the second channel switching valve 30 is placed in the connection state shown by a dotted line, solenoid valve SV1 is opened and pump 82 is driven. As a result, sample gas contained in the sample container, such as a sample bag, is suctioned via channel F1 connected to port a of first channel switching valve 20, passes through collection tube 51 and metering tube 40 and is discharged through gas outlet 71. The rest of the operation is the same as in the example of embodiment described above.

DESCRIPTION OF REFERENCES

1 . . . Sample introduction unit
2 . . . Analysis unit
3 . . . Control unit
SV1 through 3 . . . Solenoid valve
T1, T2 . . . Branch tube
10 . . . Needle
11 . . . Sample container
20 . . . First channel switching valve
30 . . . Second channel switching valve
40 . . . Metering tube
50 . . . Sample concentrating unit
51 . . . Collection tube
52 . . . Cooling unit
53 . . . Heating unit
61, 62, 63 . . . Gas inlet
71, 72, 73 . . . Gas outlet
91 . . . Column
92 . . . Column oven
93 . . . Detector

What is claimed is:

1. A gas sample introduction device for introducing sample gas into a gas analysis device, comprising:
   a) a metering tube having a predetermined volume;
   b) a sample gas supply channel for introducing sample gas into said metering tube;
   c) a carrier gas supply channel for introducing carrier gas into said metering tube;
   d) an evacuation channel for discharging gas which has passed through said metering tube to the outside;
   e) a concentrating means which comprises a collection tube containing an adsorbent and concentrates the sample gas through thermal desorption;
   f) a first channel changeover valve which switches between a load state in which said metering tube is interposed between said sample gas supply channel and said evacuation channel and an injection state in which said metering tube is interposed between said carrier gas supply channel and said gas analysis device; and
   g) a second channel switching valve which, in said load state and said injection state, switches between a collection tube interposition state and a collection tube shunt state,
   wherein, in said collection tube interposition state, said collection tube is interposed between said sample gas supply channel and said metering tube when said first channel changeover valve is in said load state, and
   wherein, in said collection tube shunt state, said collection tube is disconnected from said sample gas supply channel and said metering tube.

2. The gas sample introduction device as described in claim 1, further comprising:
   h) a purging gas supply channel for introducing a purging gas into said collection tube; and
   i) a purging gas discharge channel for discharging the purging gas which has passed through said collection tube to the outside,
   wherein said second channel switching valve interposes said collection tube between said purging gas supply channel and purging gas discharge channel in said collection tube shunt state.

3. The gas sample introduction device of claim 1, wherein, when said second channel switching valve is in said collection tube interposition state, said collection tube is interposed between said metering tube and said gas analysis device when said first channel changeover valve is in said injection state.

* * * * *